(12) United States Patent
Ionkin et al.

(10) Patent No.: US 7,675,228 B2
(45) Date of Patent: Mar. 9, 2010

(54) ELECTROLUMINESCENT IRIDIUM COMPOUNDS WITH SILYLATED, GERMANYLATED, AND STANNYLATED LIGANDS, AND DEVICES MADE WITH SUCH COMPOUNDS

(75) Inventors: Alex Sergey Ionkin, Kennett Square, PA (US); Ying Wang, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 879 days.

(21) Appl. No.: 11/452,776

(22) Filed: Jun. 14, 2006

(65) Prior Publication Data

US 2008/0074033 A1   Mar. 27, 2008

(51) Int. Cl.
*H01J 1/62* (2006.01)
*C09K 11/06* (2006.01)
*C07F 15/00* (2006.01)

(52) U.S. Cl. .................. 313/504; 252/301.26; 428/689; 428/690; 546/2; 546/14

(58) Field of Classification Search .................. 546/14, 546/2, 10; 428/689, 690; 313/504; 252/301.26
See application file for complete search history.

(56) References Cited

U.S. PATENT DOCUMENTS

| 5,247,190 | A | 9/1993 | Friend et al. |
| 5,408,109 | A | 4/1995 | Heeger et al. |
| 5,552,678 | A | 9/1996 | Tang et al. |
| 2002/0190250 | A1 | 12/2002 | Grushin et al. |
| 2007/0278936 | A1* | 12/2007 | Herron et al. ............... 313/504 |

FOREIGN PATENT DOCUMENTS

| EP | 443 861 B1 | 7/1995 |
| WO | WO 02/02714 A2 | 1/2002 |

OTHER PUBLICATIONS

Baldo et. al., Very High-Efficiency Green Organic Light-Emitting Devices Based on Electrophosphorescence, Appl. Phys. Lett., 1999, vol. 75:4-6.
Djurovich et. al., Ir (III) Cyclometalated Complexes as Efficient Phosphorescent Emitters in Polymer Blend and Organic LED, Polymer Preprints, 2000, vol. 41:770-771.

* cited by examiner

*Primary Examiner*—Charanjit S Aulakh

(57) ABSTRACT

The present invention is directed to electroluminescent complexes of iridium(III) with silylated, germanylated and stannylated ligands. The invention is further directed to electronic devices in which the active layer includes an electroluminescent Ir(III) complex with silylated, germanylated and stannylated ligands.

17 Claims, 1 Drawing Sheet

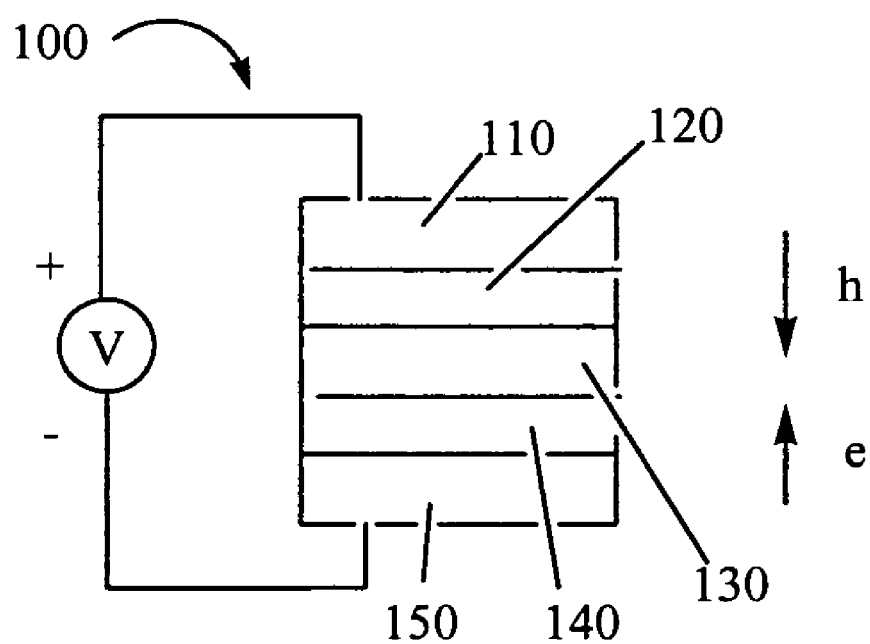
Figure 1 – Schematic of a light-emitting device

ELECTROLUMINESCENT IRIDIUM COMPOUNDS WITH SILYLATED, GERMANYLATED, AND STANNYLATED LIGANDS, AND DEVICES MADE WITH SUCH COMPOUNDS

FIELD OF THE INVENTION

The present invention is directed to electroluminescent complexes of iridium(III) with silylated, germanylated and stannylated ligands. The invention is further directed to electronic devices in which the active layer includes an electroluminescent Ir(III) complex with silylated, germanylated and stannylated ligands.

BACKGROUND

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in U.S. Pat. Nos. 5,247,190, 5,408,109, and EP443 861. Complexes of 8-hydroxyquinolate with trivalent metal ions, particularly aluminum, have been extensively used as electroluminescent components, as has been disclosed in U.S. Pat. No. 5,552,678.

US 2002/0190250 discloses electroluminescent iridium compounds with fluorinated phenylpyridines, and devices made with such compounds.

Burrows and Thompson have reported that fac-tris(2-phenylpyridine) iridium can be used as the active component in organic light-emitting devices (*Appl. Phys. Lett.* 1999, 75, 4.). The performance is maximized when the iridium compound is present in a host conductive material. Thompson has further reported devices in which the active layer is poly(N-vinyl carbazole) doped with fac-tris[2-(4',5'-difluorophenyl)pyridine-$C^{'2}$,N]iridium(III) (Polymer Preprints 2000, 41(1), 770). Electroluminescent iridium complexes having fluorinated phenylpyridine, phenylpyrimidine, or phenylquinoline ligands have been disclosed in WO 02/02714.

However, there is a continuing need for electroluminescent compounds.

SUMMARY OF THE INVENTION

One aspect of this invention is a composition represented by Formula I:

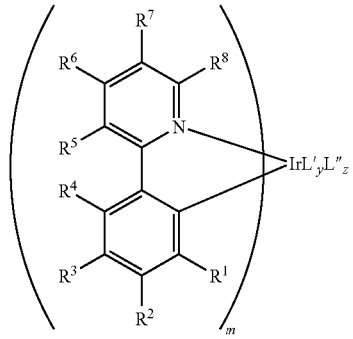

Formula I wherein:
$R^1, R^2, R^3, R^4 R^5, R^6, R^7$ and $R^8$ are independently selected from the group consisting of H, F, alkyl, aryl, fluoroalkyl, fluoroaryl, and $E(R^9)_3$ groups wherein E is Si, Ge, or Sn, wherein at least one of $R^1, R^2, R^3, R^4, R^5, R^6, R^7$ and $R^8$ is $E(R^9)_3$;

any two adjacent members of $R^1, R^2, R^3, R^4 R^5, R^6, R^7$ and $R^8$ may be taken together to form 5- or 6-membered rings; and $R^9$ is an alkyl or aryl group or $E(alkyl)_3$, $E(alkyl)_2(aryl)$, $E(alkyl)(aryl)_2$ or $E(aryl)_3$;

L'=a bidentate ligand selected from the group consisting of beta-diketonates, beta-diketiminates, beta-hydroxyphosphines, alpha-hydroxyamines and beta-hydroxyamines;

L''=a monodentate ligand selected from the group consisting of hydride, CO, nitrites, isonitriles, olefins, acetylenes, phosphines, arsines, amines, and halides;

m=1, 2 or 3;

y=0, 1 or 2, and z=0, 2 or 4, wherein the compound is charge-neutral and the iridium is hexacoordinate.

Another aspect of the present invention is a substituted 2-phenylpyridine, phenylquinoline or phenylisoquinoline having Formula II below:

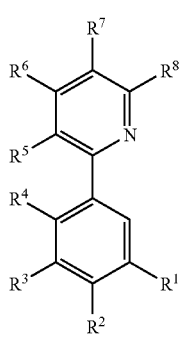

Formula II where $R^1$-$R^8$ are as defined above.

A further aspect of the present invention is an electronic device having at least one emitting layer comprising at least one Ir(III) compound of Formula I

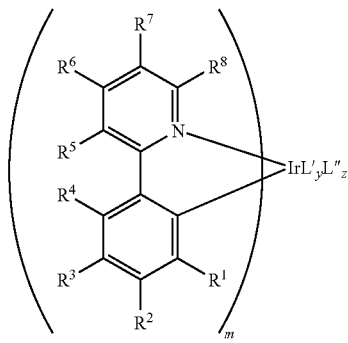

Formula I wherein:
$R^1, R^2, R^3, R^4 R^5, R^6, R^7$ and $R^8$ are independently selected from the group consisting of H, F, alkyl, aryl, fluoroalkyl, fluoroaryl, and $E(R^9)_3$ groups wherein E is Si, Ge, or Sn, wherein at least one of $R^1, R^2, R^3, R^4, R^5, R^6, R^7$ and $R^8$ is $E(R^9)_3$;

any two adjacent members of $R^1, R^2, R^3, R^4 R^5, R^6, R^7$ and $R^8$ may be taken together to form 5- or 6-membered rings; and $R^9$ is an alkyl or aryl group or $E(alkyl)_3$, $E(alkyl)_2(aryl)$, $E(alkyl)(aryl)_2$ or $E(aryl)_3$;

L'=a bidentate ligand selected from the group consisting of beta-diketonates, beta-diketiminates, beta-hydroxyphosphines, alpha-hydroxyamines and beta-hydroxyamines;

L"=a monodentate ligand selected from the group consisting of hydride, CO, nitriles, isonitriles, olefins, acetylenes, phosphines, arsines, amines, and halides;

m=1, 2 or 3;
y=0, 1 or 2, and
z=0, 2 or 4, wherein the compound is charge-neutral and the iridium is hexacoordinate.

A further aspect of the invention is a process for preparing complexes of Formula VI

Formula VI comprising reacting iridium trichloride hydrate with L in a solvent comprising methylphosphate, wherein L is a phenylpyridine, phenylquinoline or phenylisoquinoline ligand; and Z is Cl or $OR^{16}$, where $R^{16}$ is H, $CH_3$, or $C_2H_5$.

DESCRIPTION OF THE DRAWINGS

FIG. 1 is a schematic diagram of a light-emitting device (LED).

DETAILED DESCRIPTION

The term "ligand" means a molecule, ion, or atom that is attached to the coordination sphere of a metallic ion. The term "complex", when used as a noun, means a compound having at least one metallic ion and at least one ligand. The term "group" means a part of a compound, such a substituent in an organic compound or a ligand in a complex. The term "facial" means one isomer of a complex, $Ma_3b_3$, where "a" and "b" represent different coordinating atoms, having octahedral geometry, in which the three "a" atoms are all adjacent, i.e. at the corners of one face of the octahedron. The term "meridional" means one isomer of a complex, $Ma_3b_3$, having octahedral geometry, in which the three "a" atoms occupy three positions such that two are trans to each other. The term "hexacoordinate" means that six groups or points of attachment are coordinated to a central metal. The phrase "adjacent to," when used to refer to layers in a device does not necessarily mean that one layer directly contacts another layer. The phrase "adjacent R groups" is used to refer to R groups that are next to each other in a chemical formula (i.e., R groups that are on atoms joined by a bond). The term "photoactive" refers to any material that exhibits electroluminescence and/or photosensitivity. In the Formulae and Equations, the letters L, R, Y, and Z are used to designate atoms or groups, which are defined within. All other letters are used to designate conventional atomic symbols. The term "alkylaryl" denotes an alkyl-substituted aryl group.

As used herein with regard to groups within chemical formulas, "alkyl" refers to saturated hydrocarbon chains. Preferred alkyl groups include those having carbon chain lengths of 1 to 20 carbons, more preferably 1 to 10 carbon atoms. Examples of preferred alkyl groups include methyl, ethyl, propyl, iso-propyl, butyl, iso-butyl, t-butyl, neo-pentyl, neo-octyl As used herein with regard to groups within chemical formulas, "aryl" refers to moieties comprising at least one aromatic ring, which can be substituted or unsubstituted. An aryl can have one or more aromatic rings that can be fused, connected by single bonds or other groups. Examples of substituent groups that can be on substituted aromatic rings in the compounds having the formulas disclosed herein include C1-C20 alkyl, C6-C10 aryl, silyl, F, Cl and Br.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

In one embodiment, the present invention is directed to iridium compounds (generally referred as "Ir(III) compounds") represented by Formula I:

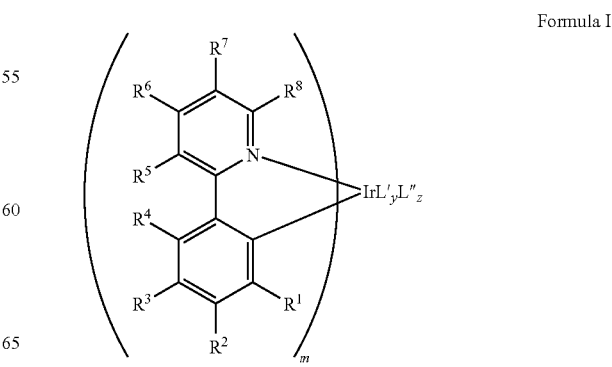

Formula I wherein:

R$^1$, R$^2$, R$^3$, R$^4$ R$^5$, R$^6$, R$^7$ and R$^8$ are independently selected from the group consisting of H, F, alkyl, aryl, fluoroalkyl, fluoroaryl, and E(R$^9$)$_3$ groups wherein E is Si, Ge, or Sn, wherein at least one of R$^1$, R$^2$, R$^3$, R$^4$, R$^5$, R$^6$, R$^7$ and R$^8$ is E(R$^9$)$_3$;

any two adjacent members of R$^1$, R$^2$, R$^3$, R$^4$ R$^5$, R$^6$, R$^7$ and R$^8$ may be taken together to form 5- or 6-membered rings; and R$^9$ is an alkyl or aryl group or E(alkyl)$_3$, E(alkyl)$_2$(aryl), E(alkyl)(aryl)$_2$ or E(aryl)$_3$;

L'=a bidentate ligand selected from the group consisting of beta-diketonates, beta-diketiminates, beta-hydroxyphosphines, alpha-hydroxyamines and beta-hydroxyamines;

L"=a monodentate ligand selected from the group consisting of hydride, CO, nitriles, isonitriles, olefins, acetylenes, phosphines, arsines, amines, and halides;

m=1, 2 or 3, y=0, 1 or 2, and z=0, 2 or 4.

The compound is charge-neutral and the iridium is hexacoordinate.

The alkyl and aryl groups of R$^1$-R$^9$ can be optionally partially or completely fluorinated.

In one embodiment of this invention, R$^1$, R$^3$ and R$^4$ are H, and R$^2$ is Si(alkyl)$_3$, preferably SiMe$_3$. Alternatively, R$^1$, R$^2$ and R$^4$ are H, and R$^3$ is Si(alkyl)$_3$, preferably SiMe$_3$.

In one embodiment of this invention, R$^5$ and R$^8$ are H, and R$^6$ and R$^7$ are H or alkyl, preferably H or Me. In another embodiment, R$^5$ and R$^6$ taken together are —CH═CH—CH═CH— or alkyl-substituted derivatives thereof, and are part of a 6-membered aromatic ring.

In one embodiment of a compound of Formula I, L' ligand is a monoanionic bidentate ligand. In general these ligands have N, O, P, or S as coordinating atoms and form 5- or 6-membered rings when coordinated to the iridium. Suitable coordinating groups include amino, imino, amido, alkoxide, carboxylate, phosphino, and thiolate. Examples of suitable parent compounds for these ligands include β-dicarbonyls (for β-enolate ligands), and their N and S analogs; amino carboxylic acids (for aminocarboxylate ligands); pyridine carboxylic acids (for iminocarboxylate ligands); salicylic acid derivatives (for salicylate ligands); hydroxyquinolines (for hydroxyquinolinate ligands) and their S analogs; and phosphinoalkanols (for phosphinoalkoxide ligands).

The β-enolate ligands generally have the Formula III

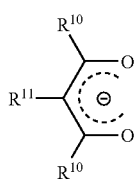

Formula III where R$^{10}$ is the same or different at each occurrence. The R$^{10}$ groups can be substituted or unsubstituted alkyl, aryl, alkylaryl or heterocyclic groups. Adjacent R$^{10}$ and R$^{11}$ groups can be joined to form five- and six-membered rings, which can be substituted. In one embodiment, R$^{10}$ groups are selected from the group consisting of —C$_n$(F)$_{2n+1}$, —C$_6$H$_5$, cyclo-C$_4$H$_3$S, and cyclo-C$_4$H$_3$O, where n is an integer from 1 through 20.

The R$^{11}$ group can be H, F, substituted or unsubstituted alkyl, aryl, alkylaryl, or a heterocyclic group.

Examples of suitable β-enolate ligands include the compounds listed below. The abbreviation for each β-enolate example is given below in brackets.

2,4-pentanedionate [acac]

1,3-diphenyl-1,3-propanedionate [DI]

2,2,6,6-tetramethyl-3,5-heptanedionate [TMH]

4,4,4-trifluoro-1-(2-thienyl)-1,3-butanedionate [TTFA]

7,7-dimethyl-1,1,1,2,2,3,3-heptafluoro-4,6-octanedionate [FOD]

1,1,1,3,5,5,5-heptafluoro-2,4-pentanedionate [F7acac]

1,1,1,5,5,5-hexafluoro-2,4-pentanedionate [F6acac]

1-phenyl-3-methyl-4-i-butyryl-pyrazolinonate [FMBP]

The β-dicarbonyl parent compounds are generally available commercially. The parent compound 1,1,1,3,5,5,5-heptafluoro-2,4-pentanedione, CF$_3$C(O)CFHC(O)CF$_3$, can be prepared using a two-step synthesis, based on the reaction of perfluoropentene-2 with ammonia, followed by a hydrolysis step, according to the procedure published in *Izv. AN USSR. Ser. Khim.* 1980, 2827. This compound should be stored and reacted under anhydrous conditions, as it is susceptible to hydrolysis. General methods for preparing β-dicarbonyl compounds have been disclosed by T. J. Sommer, (Synthesis (2004), (2), 161-201) and T. M. Harris et al. (Organic Reactions (New York) (1969), 17, 155-211).

The hydroxyquinolinate ligands can be substituted with groups such as alkyl or alkoxy groups that can be partially or fully fluorinated. Examples of suitable hydroxyquinolinate ligands include (with abbreviation provided in brackets):

8-hydroxyquinolinate [8hq]

2-methyl-8-hydroxyquinolinate [Me-8hq]

10-hydroxybenzoquinolinate [10-hbq]

The parent hydroxyquinoline compounds are generally available commercially. General methods for preparing hydroxyquinolate compounds have been disclosed by Y. Hamada (IEEE Transactions on Electron Devices (1997), 44(8), 1208-1217) and M. Glasbeek (Topics in Current Chemistry (2001), 213 (Transition Metal and Rare Earth Compounds), 95-142).

Phosphino alkoxide ligands generally have Formula IV:

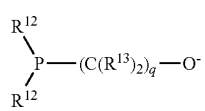

Formula IV where

R$^{13}$ can be the same or different at each occurrence and is selected from the group consisting of H and C$_n$(F)$_{2n+1}$, R$^{12}$ can be the same or different at each occurrence and is selected from the group consisting of C$_n$(F)$_{2n+1}$, C$_6$(F)$_5$, C$_6$H$_{5-n}$(R$^{14}$)$_n$, and (CH$_2$)$_n$C(C$_n$(F)$_{2n+1}$)$_2$OH;

R$^{14}$ is selected from the group consisting of CF$_3$, C$_2$F$_5$, n-C$_3$F$_7$, i-C$_3$F$_7$, C$_4$F$_9$, and CF$_3$SO$_2$;

n is an integer independently selected from 0-5; and q is 2 or 3.

Examples of suitable phosphino alkoxide ligands include (with abbreviation provided in brackets):

3-(diphenylphosphino)-1-oxypropane [dppO]

1,1-bis(trifluoromethyl)-2-(diphenylphosphino)-ethoxide [ffmdpeO]

The parent phosphino alkanol compounds are available commercially, or can be prepared using known procedures, such as, for example, the procedure reported for tfmdpeO in *Inorg. Chem.* 1985, v.24, p. 3680 or in *J. Fluorine Chem.* 2002, 117, 121.

In one embodiment, L' is a ligand coordinated through a carbon atom which is part of an aromatic group. The ligand can have Formula V:

Ar[—(CH$_2$)$_r$—Y]$_p$   Formula V wherein Ar is an aryl or heteroaryl group, Y is a group having a heteroatom capable of coordinating to Ir, r is 0 or an integer from 1 through 20, and p is an integer from 1 through 5, wherein one or more of the carbon units in (CH$_2$)$_r$ can be replaced with a heteroatom (e.g., NH or O or S), and the proviso that one or more of the hydrogens in (CH$_2$)$_r$ can be replaced with D or F.

In one embodiment of this invention, Y is selected from N(R$^{14}$)$_2$, OR$^{14}$, SR$^{14}$, and P(R$^{15}$)$_2$, wherein R$^{14}$ is the same or different at each occurrence and is selected from the group consisting of H, C$_n$H$_{2n+1}$ and C$_n$(F)$_{2n+1}$, and R$^{15}$ is the same or different at each occurrence and is selected from the group consisting of H, R$^{14}$, Ar and substituted Ar.

In one embodiment of this invention, Ar is phenyl, r is 1, Y is P(Ar)$_2$, and p is 1 or 2.

Monodentate ligand L" can be anionic or nonionic. Anionic ligands include, but are not limited to, H—("hydride") and ligands having C, O or S as coordinating atoms. Coordinating groups include, but are not limited to alkoxides, carboxylates, thiocarboxylates, dithiocarboxylates, sulfonates, thiolates, carbamates, dithiocarbamates, thiocarbazone anions, or sulfonamide anions. In some cases, ligands listed above as L', such as β-enolates and phosphinoalkoxides, can act as monodentate ligands. The monodentate ligand can also be a coordinating anion such as halide, nitrate, sulfate, or hexahaloantimonate.

The monodentate L" ligand can also be a non-ionic ligand, such as CO or a monodentate phosphine ligand. The phosphine ligands can have Formula VII PAr'$_3$   Formula VII where Ar' represents an aryl or heteroaryl group. The Ar' group can be unsubstituted, or substituted with alkyl, heteroalkyl, aryl, heteroaryl, halide, carboxyl, sulfoxyl, or amino groups.

In one embodiment of Formula I, the compound is tris-cyclometallated, with m=3 and y=z=0. The compound can be facial, meridional, or a mixture of isomers.

In one embodiment of Formula I, m=2. In one embodiment, y=1 and z=0.

In one embodiment of Formula I, m=1. In one embodiment y=1 and z=2. In one embodiment, one L" ligand is a hydride and one L' ligand is nonionic. In one embodiment, L' is a ligand coordinated through a carbon atom which is part of an aromatic group.

In one embodiment, the complexes having Formula I exhibit red or green luminescence. In one embodiment, the complexes have photoluminescent and/or electroluminescent spectra that have a maximum between 490 nm and 750 nm.

Examples of iridium complexes having Formula I include:

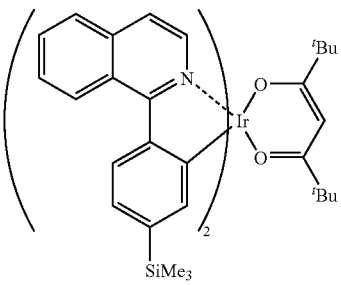

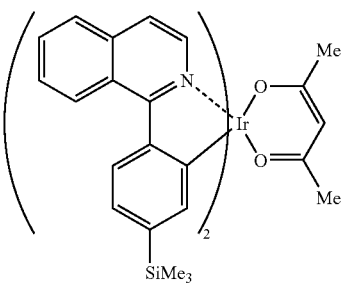

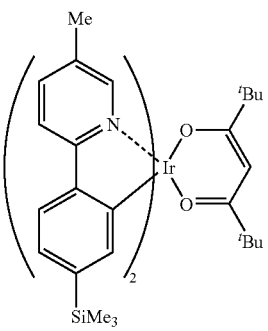

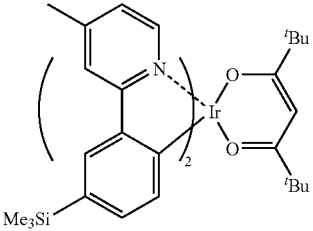

The Ir(III) compounds of this invention are neutral and non-ionic, and can be sublimed intact. Thin films of these materials obtained via sublimation or vacuum deposition exhibit good to excellent electroluminescent properties. Introduction of fluorine substituents into the ligands on the iridium atom increases both the stability and volatility of the complexes. As a result, vacuum deposition can be carried out at lower temperatures and decomposition of the complexes can be avoided. Introduction of fluorine substituents into the ligands can often reduce the non-radiative decay rate and the self-quenching phenomenon in the solid state. These reductions can lead to enhanced luminescence efficiency.

One embodiment of the present invention is compositions of Formula II (also referred to as substituted 2-phenylpyridine, phenylquinoline or phenylisoquinoline precursor compounds)

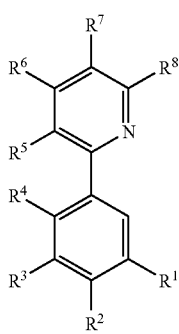

Formula II wherein $R^1$, $R^2$, $R^3$, $R^4$ $R^5$, $R^6$, $R^7$ and $R^8$ are independently selected from the group consisting of H, F, alkyl, aryl, fluoroalkyl, fluoroaryl, and $E(R^9)_3$ groups wherein E is Si, Ge, or Sn, wherein at least one of $R^1$, $R^2$, $R^3$, $R^4$ $R^5$, $R^6$, $R^7$ and $R^8$ is $E(R^9)_3$;

any two adjacent members of $R^1$, $R^2$, $R^4$ $R^5$, $R^6$, $R^7$ and $R^8$ may be taken together to form 5- or 6-membered rings; and $R^9$ is selected from an alkyl or aryl group or $E(alkyl)_3$, $E(alkyl)_2(aryl)$, $E(alkyl)(aryl)_2$ or $E(aryl)_3$.

The compositions of Formula II are useful for making the Ir(III) compounds of Formula I.

Examples of compositions of Formula II include trimethylsilyl derivatives of 2-phenylpyridine and related compounds, as illustrated by Structures I-III:

Structure I

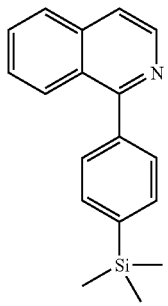

Structure II

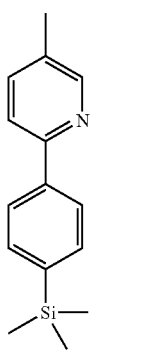

Structure III

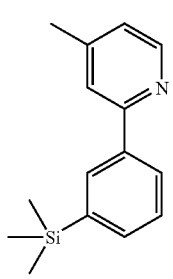

There is free rotation about the bond between the two aromatic ring systems. However, for the discussion herein, the compounds are described in terms of one orientation.

The substituted 2-phenylpyridines and related compounds, as shown in Formula II above, can be prepared, for example using the Suzuki coupling of the substituted 2-chloropyridine (or chloroquinoline or choloroisoquinoline) with arylboronic acid, as described in O. Lohse, P. Thevenin, E. Waldvogel *Synlett,* 1999, 45-48. 2-Phenylpyridines can be prepared via pyrylium chemistry, as described in Spitzner, D. Product class 1: pyridines. Science of Synthesis (2005), 15, 11-284.

The 2-phenylpyridines and related compounds can be used for the synthesis of cyclometalated iridium complexes. One synthetic method uses commercially available iridium trichloride hydrate and silver trifluoroacetate. The reactions are generally carried out with an excess of the appropriate 2-phenylpyridine (or pyrimidine or quinoline), without a solvent, in the presence of 3 equivalents of $AgOCOCF_3$. This reaction is illustrated in Equation (1) below:

Eq. 1

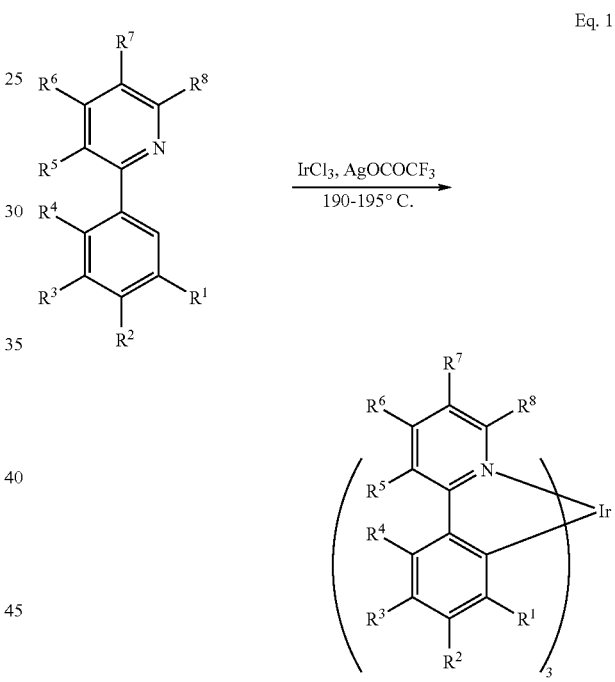

Tris-cyclometalated iridium complexes having Formula I where m=3, can be isolated, purified, and fully characterized by elemental analysis, $^1H$ and $^{19}F$ NMR spectral data, and, for selected compounds, single crystal X-ray diffraction. In some cases, mixtures of isomers are obtained. Often the mixture can be used without isolating the individual isomers.

Bis-cyclometalated iridium complexes having Formula I where m=2, can, in some cases, be isolated from the reaction mixture using the same synthetic procedures as preparing the tris-cyclometalated complexes above. The bis-cyclometalated complexes can also be prepared by first preparing an intermediate iridium dimer

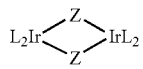

where each L can be the same or different at each occurrence, and each L is a phenylpyridine, phenylquinoline or phenylisoquinoline ligand, and Z is Cl or $OR^{16}$, where $R^{16}$ is H, $CH_3$, or $C_2H_5$. The iridium dimers can generally be prepared by first reacting iridium trichloride hydrate with the 2-phenylpyridine and optionally adding $NaOR^{16}$.

In one embodiment of the invention, an improved process for preparing bis-cyclometalated iridium complexes is provided. The chloro-bridged iridium dimer is prepared by reacting iridium (III) chloride trihydrate with the appropriate ligand precursor in trimethylphosphate.

Mono-cyclometalated iridium complexes of the invention can, in some cases, be isolated from reaction mixtures formed by the above-described rocesses. Such mono-cyclometalated species can be favored by use of phosphine-containing ligands such as that shown in Formula VII and by using a stoichiometric excess of such ligands (>2 equivalents per Ir). These materials can be isolated from the reaction mixture by standard techniques, such as chromatography on silica with methylene chloride as eluent.

Another embodiment of this invention is an electronic device comprising at least one photoactive layer positioned between two electrical contact layers, wherein the at least one layer of the device includes the iridium complex of Formula I. Devices frequently have additional hole-transport and electron-transport layers. A typical structure is shown in FIG. 1. The device 100 has an anode layer 110 and a cathode layer 150. Adjacent to the anode is a layer 120 comprising hole-transport material. Adjacent to the cathode is a layer 140 comprising an electron-transport material. Between the hole-transport layer and the electron-transport layer is the photoactive layer 130.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, phototubes, and photovoltaic cells, as these terms are described by John Markus in *Electronics and Nucleonics Dictionary*, 470 and 476 (McGraw-Hill, Inc. 1966).

The iridium compounds of the Formula I are particularly useful as the photoactive material in layer 130, or as electron-transport material in layer 140. The iridium complexes of the invention can be used as the light-emitting material in diodes. Additional materials can be present in the emitting layer with the iridium compound. A diluent or host material can also be added. Suitable diluents include charge transport materials, processing aids and inert matrix materials. The diluent can include polymeric materials, small molecules or mixtures thereof. The diluent may improve the physical or electrical properties of films containing the iridium compound, may decrease self-quenching in the iridium compounds described herein, and/or may decrease the aggregation of the iridium compounds described herein. Non-limiting examples of suitable polymeric materials include poly(N-vinyl carbazole) and polysilane. Non-limiting examples of suitable small molecules includes 4,4'-N,N'-dicarbazole biphenyl and tertiary aromatic amines. When a diluent is used, the iridium compound is generally present in a small amount. In one embodiment, the amount of iridium compound in the photoactive layer is less than 20% by weight, based on the total weight of the layer; in another embodiment, the iridium compound is less than 10% by weight.

In some embodiments, the iridium complexes may be present in more than one isomeric form, or mixtures of different complexes may be present. As used herein, the term "the iridium compound" encompasses mixtures of compounds and/or isomers.

The other layers in the OLED can be made of any materials suitable for use in each of such layers. The anode 110, is an electrode that is particularly efficient for injecting positive charge carriers. For example, it can be made of materials containing a metal, mixed metals, alloys, metal oxides or mixed-metal oxides, or it can be a conducting polymer. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The IUPAC numbering system is used throughout, where the groups from the Periodic Table are numbered from left to right as 1-18 (CRC Handbook of Chemistry and Physics, $81^{st}$ Edition, 2000). The anode 110 may also comprise an organic material such as polyaniline, as disclosed in "Flexible light-emitting diodes made from soluble conducting polymer," *Nature* vol. 357, pp 477-479 (11 Jun. 1992). At least one of the anode and cathode is desirably at least partially transparent to allow the generated light to be observed.

Examples of hole-transport materials for layer 120 have been summarized for example, in Kirk-Othmer Encyclopedia of Chemical Technology, Fourth Edition, Vol. 18, p. 837-860, 1996, by Y. Wang. Both hole-transporting molecules and polymers can be used. Commonly used hole-transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), and porphyrinic compounds, such as copper phthalocyanine. Commonly used hole-transporting polymers are polyvinylcarbazole, (phenylmethyl)polysilane, and polyaniline. It is also possible to obtain hole-transporting polymers by doping hole-transporting molecules such as those mentioned above into polymers such as polystyrene and polycarbonate.

Examples of electron-transport materials for layer 140 include metal chelated oxinoid compounds, such as tris(8-hydroxyquinolato)aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). Layer 140 can function both to facilitate electron-transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds can also be deposited between the organic layer and the cathode layer to lower the operating voltage.

It is known to have other layers in organic electronic devices. For example, there can be a layer (not shown) between the conductive polymer layer 120 and the active layer 130 to facilitate positive charge transport and/or band-gap matching of the layers, or to function as a protective layer. Similarly, there can be additional layers (not shown) between the active layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the conductive polymer layer 120, the active layer 130, and cathode layer 150, can be surface-treated to increase charge carrier transport efficiency. The choice of materials for each of the component layers is preferably determined by balancing the goals of providing a device with high device efficiency. Each functional layer can be made up of more than one layer.

The device can be prepared by sequentially vapor-depositing the individual layers on a suitable substrate. Substrates such as glass and polymeric films can be used. Conventional vapor deposition techniques can be used, such as thermal evaporation and chemical vapor deposition. Alternatively, the organic layers can be coated from solutions or dispersions in suitable solvents, using any conventional coating technique. In general, the different layers will have the following range of thicknesses: anode 110, 500-5000 Å, preferably 1000-2000 Å; hole-transport layer 120, 50-1000 Å, preferably 200-800 Å; light-emitting layer 130, 10-1000 Å, preferably 100-800 Å; electron-transport layer 140, 50-1000 Å, preferably 200-800 Å; cathode 150, 200-10000 Å, preferably 300-5000 Å. The location of the electron-hole recombination zone in the device, and thus the emission spectrum of the device, can be affected by the relative thickness of each layer. Thus the thickness of the electron-transport layer is desirably chosen so that the electron-hole recombination zone is in the light-emitting layer. The desired ratio of layer thicknesses can be determined by one skilled in the art, based on the nature of the materials used.

The efficiency of devices made with the iridium compounds disclosed herein can be further improved by optimizing the other layers in the device. For example, more efficient cathodes such as Ca, Ba or LiF can be used. Shaped substrates and novel hole-transport materials that result in a reduction in operating voltage or increase quantum efficiency are also applicable. Additional layers can also be added to tailor the energy levels of the various layers and facilitate electroluminescence.

The iridium complexes are photoluminescent and may be useful in applications other than OLEDs. For example, organometallic complexes of iridium have been used as oxygen sensitive indicators, as phosphorescent indicators in bioassays, and as catalysts. The bis-cyclometalated complexes can be used to sythesize tris-cyclometalated complexes where the third ligand is the same or different. The first two cyclometalations generally take place more readily than the third; the first two cyclometalated ligands are usually the same and third one can be different.

EXAMPLES

The following examples illustrate certain features and advantages of the present invention. They are intended to be illustrative of the invention, but not limiting. All percentages are by weight, unless otherwise indicated.

The following chemicals used in the Examples below were purchased from Sigma-Aldrich Inc. (St. Louis, Mo.): 4-trimethylsilyl-phenylboronic acid; 3-trimethylsilyl-phenylboronic acid; 1-chloro-isoquinoline; cesium carbonate; tris (dibenzylideneacetone)dipalladium(0); 2,2,6,6-tetramethyl-heptane-3,5-dione; 2-bromo-5-methylpyridine; 2-bromo-4-methylpyridine; trimethylphosphate; "AlQ"; and "DPA". The iridium(III) chloride trihydrate used in the Examples below was purchased from Alfa Aesar (Ward Hill, Mass.). The following chemicals used in the Examples below were purchased from Strem Chemicals, Inc. (Newburyport, Mass.): lithium 2,4-pentanedionate; and lithium (2,2,6,6-tetramethyl-3,5-heptanedionate). The preparation of MPMP is disclosed in U.S. Pat. No. 3,739,000.

Di-tert-butyl-trimethylsilylmethyl-phosphane ($^t$Bu$_2$P—CH$_2$—SiMe$_3$) was prepared as follows: 50.00 g (0.277 mol) of di-tert-butylchlorophosphine, 304 ml of a 1.0 M pentane solution of (trimethylsilylmethyl)lithium and 150 ml of THF were refluxed under argon for 3 days. The reaction mixture was allowed to cool to room temperature, and then an aqueous solution of ammonium chloride was added slowly. The organic phase was separated, and dried over magnesium sulfate. After removal of the solvent, the product was purified by distillation in vacuum. The yield of di-tert-butyl-trimethylsilanylmethyl-phosphane was 55.32 g (86%) with b.p. 50-52° C./0.5 mm. $^{31}$P-NMR (C$_6$D$_6$)+20.05 ppm. 1 H NMR (C$_6$D$_6$) 0.01 (s, 9H, SiMe$_3$), 0.23 (d, 2H, $^2$J$_{PH}$=5.34 Hz, P—CH$_2$—SiMe$_3$), 0.91 (s, 9H, Me$_3$C), 0.93 (s, 9H, Me$_3$C). Anal. Found: C, 61.89; H, 12.53; P, 13.25.

Benzyl-di-tert-butyl-phosphane ($^t$Bu$_2$P—CH$_2$-Ph) was prepared as follows: Di-tert-butylchlorophosphine (75.0 g (0.415 mole)) and 0.5 mole of a 12M solution of benzylmagnesium chloride in THF (200 ml) were refluxed under argon for 2 days. The reaction mixture was allowed to cool to room temperature, and then an aqueous solution of ammonium chloride was added slowly. The organic phase was separated, and dried over magnesium sulfate. After removal of the solvent, the product was purified by distillation in vacuum. The yield of benzyl-di-tert-butyl-phosphane was 94.3 g (96%) with b.p. 56-59° C./0.1 mm. $^{31}$P-NMR (CDCl$_3$)+36.63 ppm. 1H NMR (CDCl$_3$) 1.18 (s, 9H, Me$_3$C), 1.20 (s, 9H, Me$_3$C), 2.90 (d, $^2J_{PH}$=2.92 Hz, P—CH$_2$-Ph), 7.1-7.6 (m, 5H, aromatic protons). Anal. Found: C, 76.15; H, 10.58; P, 12.87.

Example 1

1-(4-Trimethylsilanyl-phenyl)-isoquinoline

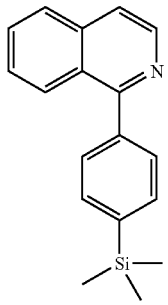

15.0 g (0.07727 mol) of 4-trimethylsilyl-phenylboronic acid, 10.11 g (0.0618 mol) 1-chloro-isoquinoline, 15.11 g (0.0464 mol) of cesium carbonate, 0.71 g (0.000775 mol) of tris(dibenzylideneacetone) dipalladium (0), 0.43 g (0.00185 mol) of di-tert-butyl-trimethylsilylmethyl-phosphane and 100 ml of dioxane were stirred at room temperature for 12 hr. The reaction mixture was filtered and the solvent was removed under vacuum. The resulting mixture was purified by chromatography on silica gel using petroleum ether/ethyl ether (10/0.5) as eluent. Yield of 1-(4-trimethylsilanyl-phenyl)-isoquinoline was 10.63 g (62%) as a colorless solid with m.p. 93.45° C. $^1$H NMR (CDCl$_3$) 0.30 (s, 9H, Me$_3$Si), 7.45-7.70 (m, 7H, arom-H), 7.85 (s, 1H, arom-H), 8.15 (s, 1H, arom-H), 8.51 (s, 1H, arom-H). Anal. Found: C, 77.68; H, 6.95; N, 4.97.

Example 2 a. Di-μ-chlorotetrakis[5-trimethylsilyl-2-(1-isoquinolinyl-κN)phenyl-κC]di-Iridium

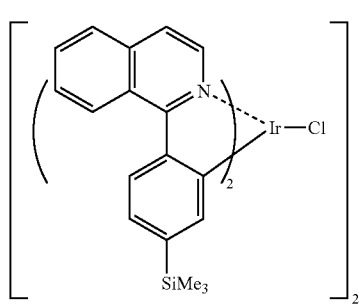

10.63 g (0.0383 mol) of 1-(4-trimethylsilanyl-phenyl)-isoquinoline, 5.06 g (0.0144 mol) of iridium (III) chloride trihydrate, 30 ml of trimethylphosphate was stirred at 90° C. for 6 hr under the flow of nitrogen. The precipitate was filtered and dried under 1.0 mm vacuum. The yield of the dimer was 9.90 g (88.37%) as a red powder. The crude above chlorodimer was used "as it is" in the next step (below).

b. Bis[5-trimethylsilyl-2-(1-isoquinolinyl-κN)phenyl-κC](2,2,6,6-tetramethyl-3,5-heptanedionato-κO, κO')-iridium

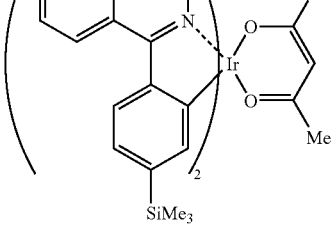

5.0 g (0.00320 mol) of di-μ-chlorotetrakis[5-trimethylsilyl-2-(1-isoquinolinyl-κN)phenyl-κC]di-iridium, 10.0 g (0.0543) 2,2,6,6-tetramethyl-heptane-3,5-dione, 4.0 g (0.074 mol) of sodium methoxide and 30 ml of THF were refluxed for 2 hr under Ar. The reaction mixture was poured into 200 ml of water and extracted twice with 200 ml of diethyl ether. The extracts were dried over magnesium sulfate overnight. The solvent was removed on a rotary evaporator and the residue was purified by chromatography on silica gel with petroleum ether/ethyl ether (10/0.5) as eluent. Yield of bis[5-trimethylsilyl-2-(1-isoquinolinyl-κN)phenyl-κC](2,2,6,6-tetramethyl-3,5-heptanedionato-κO,κO')-iridium was 3.76 g (63.14%) as a red solid with m.p. 292.0° C. $^1$H NMR (CD$_2$Cl$_2$) 0.05 (s, 18H, Me$_3$Si), 0.95 (s, 18H, t-Bu), 5.50 (s, 1H, H—C=), 6.20-9.50 (m, 18H, arom-H). Anal. Found: C, 60.71; H, 6.03; N, 3.14. The structure was confirmed by X-ray analysis.

Example 3

Bis[5-trimethylsilyl-2-(1-isoquinolinyl-κN)phenyl-κC](2,4-pentanedionato-κO,κO')-iridium 2.0 g (0.00128 mol) of di-μ-chlorotetrakis[5-trimethylsilyl-2-(1-isoquinolinyl-κN)phenyl-κC]di-iridium, 1.35 g (0.0127) lithium 2,4-pentanedionate, and 20 ml of THF were refluxed for 2 hr under Ar. The reaction mixture was poured into 200 ml of water and extracted twice with 200 ml of diethyl ether. The extracts were dried over magnesium sulfate overnight. The solvent was removed on a rotary evaporator and the residue was purified by chromatography on silica gel with petroleum ether/ethyl ether (10/0.5) as eluent. Yield of bis[5-trimethylsilyl-2-(1-isoquinolinyl-κN)phenyl-κC](2,4-pentanedionato-κO,κO')-iridium was 2.03 g (93.18%) as a red solid with m.p. 305.54° C. ¹H NMR (CD₂Cl₂) 0.03 (s, 18H, Me₃Si), 1.96 (s, 6H, Me), 5.30 (s, 1H, H—C=), 6.50-9.50 (m, 18H, arom-H). Anal. Found: C, 58.40; H, 5.19; N, 3.43.

Example 4

5-Methyl-2-(4-trimethylsilanyl-phenyl)-pyridine

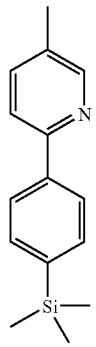

15.0 g (0.0773 mol) of 4-trimethylsilyl-phenylboronic acid, 11.96 g (0.0695 mol) of 2-bromo-5-methyl-pyridine, 15.11 g (0.0464 mol) of cesium carbonate, 0.71 g (0.000776 mol) of tris(dibenzylideneacetone) dipalladium (0), 0.43 g (0.00182 mol) of benzyl-di-tert-butyl-phosphane and 100 ml of dioxane were stirred at room temperature for 12 hr. The reaction mixture was filtered and the solvent was removed under 1 mm vacuum. The resulting mixture was purified by distillation in vacuum. Yield of 5-methyl-2-(4-trimethylsilanyl-phenyl)-pyridine was 8.05 g (48%) as a yellow solid with b.p. 111-114° C./0.02 mm and m.p. 66.07° C. ¹H NMR (CD₂Cl₂) 2.15 (s, 3H, Me) 7.45-8.50 (m, 7H, arom-H). Anal. Found: C, 74.34; H, 7.86; N, 5.85. The structure was confirmed by X-ray analysis.

Example 5 a. Di-μ-chlorotetrakis[5-trimethylsilyl-2-(4-methyl-2-pyridinyl-κN)phenyl-κC]di-iridium

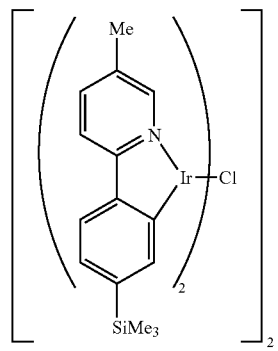

3.92 g (0.0162 mol) of 5-methyl-2-(4-trimethylsilanyl-phenyl)-pyridine, 1.72 g (0.00488 mol) of iridium (III) chloride trihydrate, and 30 ml of trimethylphosphate were stirred at room temperature for 24 hr under a flow of nitrogen. The precipitate was filtered and dried under 1.0 mm vacuum. The yield of the dimer was 1.39 g (40.17%) as a yellow powder. The crude chlorodimer was used "as it is" in the next step (below).

b. Bis[5-trimethylsilyl-2-(4-methyl-2-pyridinyl-κN)phenyl-κC](2,2,6,6-tetramethyl-3,5-heptanedionato-κO,κO')-iridium

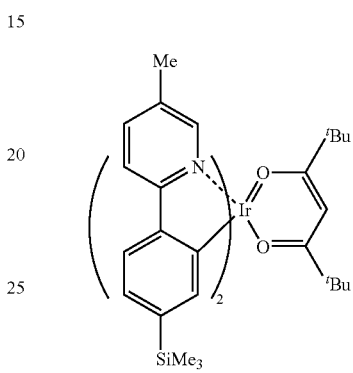

1.39 g (0.00098 mol) of di-μ-chlorotetrakis[5-trimethylsilyl-2-(4-methyl-2-pyridinyl-κN)phenyl-κC]di-iridium, 2.79 g (0.0147) lithium (2,2,6,6-tetramethyl-3,5-heptanedionate), and 40 ml of THF were refluxed for 3 hr under argon atmosphere. The reaction mixture was poured into 200 ml of water and extracted twice with 200 ml of diethyl ether. The extracts were dried over magnesium sulfate overnight. The solvent was removed on a rotary evaporator and the residue was purified by chromatography on silica gel using petroleum ether/ethyl ether (10/0.5) as eluent. Yield of bis[5-trimethylsilyl-2-(4-methyl-2-pyridinyl-κN)phenyl-κC](2,2,6,6-tetramethyl-3,5-heptanedionato-κO,κO')-iridium was 0.40 g (23.44%) as a yellow solid with m.p. 228.39° C. ¹H NMR (CD₂Cl₂) 0.05 (s, 18H, Me₃Si), 0.95 (s, 18H, t-Bu), 2.05 (s, 6H, Me), 5.10 (s, 1H, H—C=), 6.10-9.30 (m, 12H, arom-H). Anal. Found: C, 57.60; H, 6.58; N, 3.39.

Example 6

4-Methyl-2-(3-trimethylsilanyl-phenyl)-pyridine

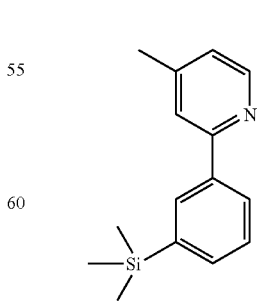

15.0 g (0.0773 mol) of 3-trimethylsilyl-phenylboronic acid, 11.96 g (0.0695 mol) of 2-bromo-4-methyl-pyridine, 30.21 g (0.0927 mol) of cesium carbonate, 0.71 g (0.000776 mol) of tris(dibenzylideneacetone) dipalladium (0), 0.38 g (0.00188 mol) of tri-tert-butyl-phosphane and 100 ml of dioxane were stirred at room temperature for 12 hr. The reaction mixture was filtered and the solvent was removed under 1 mm vacuum. The resulting mixture was purified by distillation in vacuum. Yield of 4-methyl-2-(3-trimethylsilanyl-phenyl)-pyridine was 8.18 g (48.75%) as a colorless liquid with b.p. 89-90° C./0.02. $^1$H NMR (CD$_2$Cl$_2$) 0.30 (s, 9H, Me$_3$Si), 2.32 (s, 3H, Me) 7.00-8.55 (m, 7H, arom-H). Anal. Found: C, 74.65; H, 7.94; N, 5.88.

Example 7 a. Di-μ-chlorotetrakis[4-trimethylsilyl-2-(5-methyl-2-pyridinyl-κN)phenyl-κC]di-Iridium

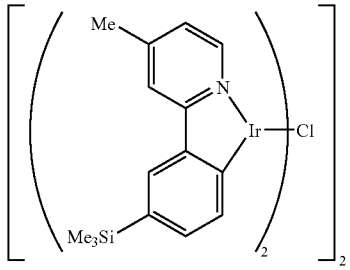

4.94 g (0.021 mol) of 4-methyl-2-(3-trimethylsilanyl-phenyl)-pyridine, 2.83 g (0.00803 mol) of iridium (III) chloride trihydrate, and 40 ml of trimethylphosphate were stirred at 110° C. for 1 hr under a flow of nitrogen. The precipitate was filtered and dried under 1.0 mm vacuum. The yield of the dimer was 1.80 g (31.69%) as a yellow powder. The crude chlorodimer was used "as it is" in the next step (below).

b. Bis[4-trimethylsilyl-2-(5-methyl-2-pyridinyl-κN)phenyl-κC](2,2,6,6-tetramethyl-3,5-heptanedionato-κO,κO')-iridium

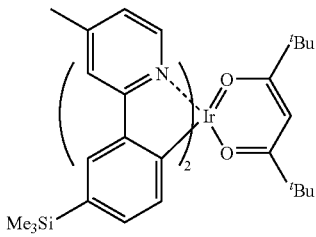

1.80 g (0.00127 mol) of di-μ-chlorotetrakis[4-trimethylsilyl-2-(5-methyl-2-pyridinyl-κN)phenyl-κC]di-iridium 5.40 g (0.0284) lithium (2,2,6,6-tetramethyl-3,5-heptanedionate), and 40 ml of THF were refluxed for 3 hr under Ar. The reaction mixture was poured into 200 ml of water and extracted twice with 200 ml of diethyl ether. The extracts were dried over magnesium sulfate overnight. The solvent was removed on a rotary evaporator and the residue was purified by chromatography on silica gel using petroleum ether/ethyl ether (10/0.5) as eluent. Yield of bis[4-trimethylsilyl-2-(5-methyl-2-pyridinyl-κN)phenyl-κC](2,2,6,6-tetramethyl-3,5-heptanedionato-κO,κO')-iridium was 1.95 g (89.45%) as a yellow solid with m.p. 226.40° C. $^1$H NMR (CD$_2$Cl$_2$) 0.05 (s, 18H, Me$_3$Si), 0.80 (s, 18H, t-Bu), 2.35 (s, 6H, Me), 5.05 (s, 1H, H—C═), 6.10-9.00 (m, 12H, arom-H). Anal. Found: C, 57.65; H, 6.49; N, 3.27. The structure was confirmed by X-ray analysis.

Example 8

OLED devices were fabricated by a thermal evaporation technique. The base vacuum for all of the thin film deposition was in the range of $10^{-6}$ torr. The deposition chamber was capable of depositing eight different films without the need to break up the vacuum.

Patterned indium tin oxide (ITO) coated glass substrates from Thin Film Devices, Inc. were used. These ITOs are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor for ~3 hr.

The cleaned, patterned ITO substrate was then loaded into the vacuum chamber and the chamber was pumped down to $10^{-6}$ torr. The substrate was then further cleaned using an oxygen plasma for about 5 min. After cleaning, multiple layers of thin films were then deposited sequentially onto the substrate by thermal evaporation. Patterned metal electrodes (Al or LiF/Al) or bipolar electrode were deposited through a mask. The thickness of the film was measured during deposition using a quartz crystal monitor (Sycon STC-200). All film thickness reported in the Examples are nominal, calculated assuming the density of the material deposited to be one. The completed OLED device was then taken out of the vacuum chamber and characterized immediately without encapsulation.

The OLED samples were characterized by measuring their (1) current-voltage (I-V) curves, (2) electroluminescence radiance versus voltage, and (3) electroluminescence spectra versus voltage The I-V curves were measured with a Source-Measurement Unit (Keithley Model 237, USA). The electroluminescence radiance (in units of cd/m$^2$) vs. voltage was measured with a luminescence meter (Minolta LS-110, Japan), while the voltage was scanned using the Keithley SMU.

The electroluminescence spectrum was obtained by collecting light using an optical fiber, through an electronic shutter, dispersed through a spectrograph, and then measured with a diode array detector. All three measurements were performed at the same time and controlled by a computer. The efficiency of the device at certain voltage is determined by dividing the electroluminescence radiance of the LED by the current density needed to run the device. The unit is in cd/A.

Table I summarizes device configuration and efficiency of OLED devices fabricated using materials disclosed in the present invention. MPMP is the hole-transport material, DPA is the electron-transport material for Emitters 2-4, and DPA/AlQ is the electron-transport material for Emitter 1. AlQ is the electron-injection material. The molecular structures of MPMP, DPA, and ALQ are shown below. The (x,y) color coordinate is based on 1931 convention.

TABLE I

Device configurations and efficiency of OLED devices

| Emitter | Device configuration | Efficiency cd/A | Radiance cd/m2 | Peak wavelength nm | Color coordinates |
|---|---|---|---|---|---|
| Emitter 1 (Red) | MPMP(302Å)/Emitter 1(402Å)/DPA(101Å)/ AlQ(304Å)/LiF(10ÅA)/ Al(505Å); | 1.4 at 11 V | 1300 at 19 V | 650 | (0.698, 0.302) |
| Emitter 2 (Red) | MPMP(303Å)/Emitter 2(402Å)/ DPA(106Å)/AlQ(302Å)/ LiF(10Å)/Al(503Å); | 1.1 at 14 V | 500 at 18 V | 640 | (0.64, 0.34) |
| Emitter 3 (Green) | MPMP(504Å)/Emitter 3(423Å)/DPA(407Å)/ LiF(10Å)/Al(716Å); | 12 at 17 V | 4000 at 20 V | 535 | (0.4, 0.6) |

TABLE I-continued
Device configurations and efficiency of OLED devices
| Emitter | Device configuration | Efficiency cd/A | Radiance cd/m2 | Peak wavelength nm | Color coordinates |
|---|---|---|---|---|---|
| Emitter 4 (Green) 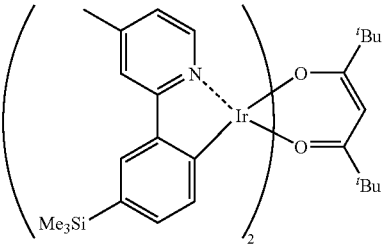 | MPMP(538Å)/Emitter 4(407Å)/DPA(413Å)/ LiF(10Å)/Al(723Å); | 6 at 22 V | 1400 at 30 V | 515 | |
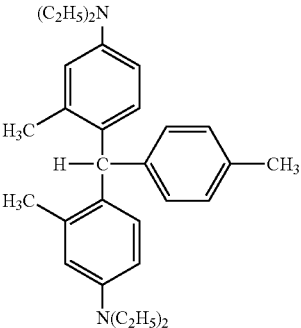
MPMP
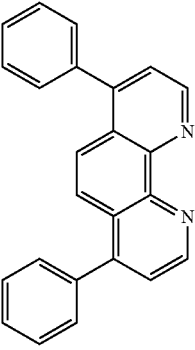
DPA
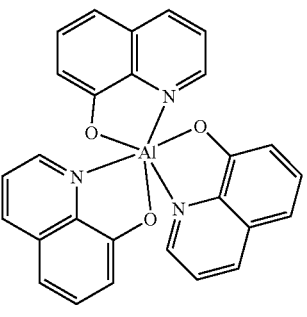
AlQ

What is claimed is:

1. An electronic device comprising at least one layer comprising a compound having Formula I:

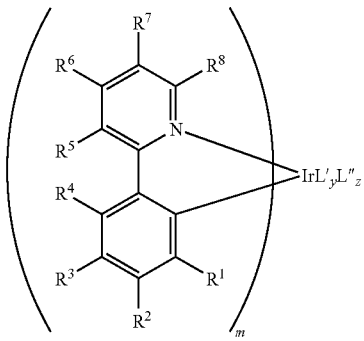

Formula I wherein:

$R^1$, $R^2$, $R^3$ and $R^4$ are independently selected from the group consisting of H, F, alkyl, aryl, fluoroalkyl, fluoroaryl, and $E(R^9)_3$ groups wherein E is Si, Ge, or Sn, wherein at least one of $R^1$, $R^2$, $R^3$, $R^4$, $R^5$, $R^6$, $R^7$ and $R^8$ is $E(R^9)_3$;

any two adjacent members of $R^1$, $R^2$, $R^3$, and $R^4$ may be taken together to form 5- or 6-membered rings; and $R^9$ is an alkyl or aryl group or $E(alkyl)_3$, $E(alkyl)_2(aryl)$, $E(alkyl)(aryl)_2$ or $E(aryl)_3$;

L'=a β-enolate ligand of Formula III

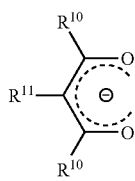

Formula III wherein $R^{10}$ is the same or different at each occurrence and is selected from the group consisting of substituted or unsubstituted alkyl, substituted or unsubstituted aryl, substituted or unsubstituted alkylaryl and substituted or unsubstituted heterocyclic groups; and $R^{11}$ is selected from the group consisting of H, F, substituted or unsubstituted alkyl, substituted or unsubstituted aryl, substituted or unsubstituted alkylaryl, and substituted or unsubstituted heterocyclic groups; or adjacent $R^{10}$ and $R^{11}$ groups are joined to form five- or six-membered rings;

L"=a monodentate ligand selected from the group consisting of hydride, CO, nitriles, isonitriles, olefins, acetylenes, phosphines, arsines, amines, and halides;

m=1, 2 or 3;

y=1 or 2, and z=0, 2 or 4, wherein the compound is charge-neutral and the iridium is hexacoordinate.

2. The device of claim 1, wherein $R^1$, $R^3$ and $R^4$=H, and $R^2$ is SiMe₃.

3. The device of claim 1, wherein $R^1$, $R^2$ and $R^4$=H, and $R^3$ is SiMe₃.

4. The device of claim 1, wherein each $R^{10}$ is independently $^tBu$ or Me and $R^{11}$ is H.

5. The device of claim 1, wherein z=2 or 4 and at least one of L" is a non-ionic ligand.

6. The device of claim 1, wherein z=2 or 4 and at least one of L" is an anionic ligand.

7. The device of claim 1, wherein the compound is selected from the group of compounds with structures VI-VII:

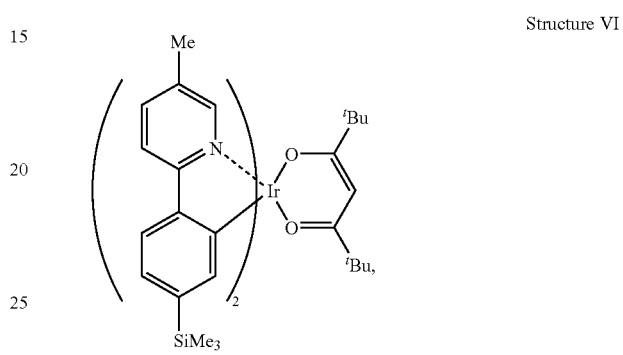

Structure VI

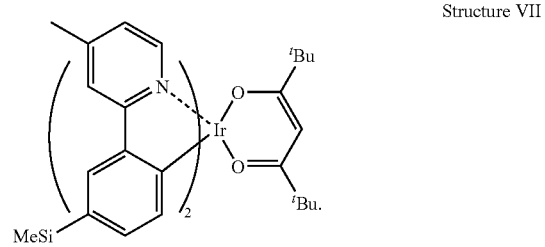

Structure VII

8. The device of claim 1, further comprising a diluent selected from the group consisting of poly(N-vinyl carbazole), polysilane, 4,4'-N,N'-dicarbazole biphenyl, and tertiary amines.

9. The device of claim 1, further comprising a hole-transport layer selected from the group consisting of: N,N'-diphenyl-N,N'-bis(3-methylphenyl)-[1,1'-biphenyl]-4,4'-diamine; 1,1-bis[(di-4-tolylamino) phenyl]cyclohexane; N,N'-bis(4-methylphenyl)-N,N'-bis(4-ethylphenyl)-[1,1'-(3,3'-dimethyl)biphenyl]-4,4'-diamine; tetrakis-(3-methylphenyl)-N,N,N',N'-2,5-phenylenediamine; α-phenyl-4-N,N-diphenylaminostyrene; p-(diethylamino)benzaldehyde diphenylhydrazone; triphenylamine; bis[4-(N,N-diethylamino)-2-methylphenyl](4-methylphenyl)methane; 1-phenyl-3-[p-(diethylamino)styryl]-5-[p-(diethylamino)phenyl]pyrazoline; 1,2-trans-bis(9H-carbazol-9-yl)cyclobutane; N,N,N',N'-tetrakis(4-methyl-phenyl)-(1,1'-biphenyl)-4,4'-diamine; porphyrinic compounds, and combinations thereof.

10. The device of claim 1, further comprising an electron-transport layer comprising compounds selected from the group consisting of tris(8-hydroxyquinolato)aluminum; 2,9-dimethyl-4,7-diphenyl-1,10-phenanthroline; 4,7-diphenyl-1,10-phenanthroline; 2-(4-biphenylyl)-5-(4-t-butylphenyl)-1,3,4-oxadiazole; 3-(4-biphenylyl)-4-phenyl-5-(4-t-butylphenyl)-1,2,4-triazole, and combinations thereof.

11. A composition represented by Formula I:

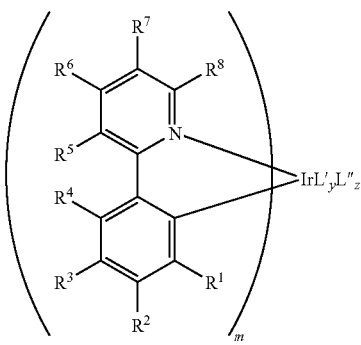

Formula I wherein:

$R^1$, $R^2$, $R^3$ and $R^4$ are independently selected from the group consisting of H, F, alkyl, aryl, fluoroalkyl, fluoroaryl, and $E(R^9)_3$ groups wherein E is Si, Ge, or Sn, wherein at least one of $R^1$, $R^2$, $R^3$, $R^4$, $R^5$, $R^6$, $R^7$ and $R^8$ is $E(R^9)_3$;

any two adjacent members of $R^1$, $R^2$, $R^3$, and $R^4$ may be taken together to form 5- or 6-membered rings; and $R^9$ is an alkyl or aryl group or $E(alkyl)_3$, $E(alkyl)_2(aryl)$, $E(alkyl)(aryl)_2$ or $E(aryl)_3$;

L'=a β-enolate ligand of Formula III

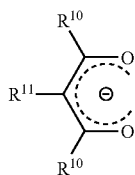

Formula III wherein $R^{10}$ is the same or different at each occurrence and is selected from the group consisting of substituted or unsubstituted alkyl, substituted or unsubstituted aryl, substituted or unsubstituted alkylaryl and substituted or unsubstituted heterocyclic groups; and $R^{11}$ is selected from the group consisting of H, F, substituted or unsubstituted alkyl, substituted or unsubstituted aryl, substituted or unsubstituted alkylaryl, and substituted or unsubstituted heterocyclic groups; or adjacent $R^{10}$ and $R^{11}$ groups are joined to form five- or six-membered rings;

L''=a monodentate ligand selected from the group consisting of hydride, GO, nitriles, isonitriles, olefins, acetylenes, phosphines, arsines, amines, and halides;

m=1, 2 or 3;
y=1 or 2, and
z=0, 2 or 4, wherein the composition is charge-neutral and the iridium is hexacoordinate.

12. The composition of claim 11, wherein $R^1$, $R^3$ and $R^4$=H, and $R^2$ is $SiMe_3$.

13. The composition of claim 11, wherein $R^1$, $R^2$ and $R^4$=H, and $R^3$ is $SiMe_3$.

14. The composition of claim 11, wherein each $R^{10}$ is $^tBu$ or Me and $R^{11}$ is H.

15. The composition of claim 11, wherein z=2 or 4 and at least one of L'' is a non-ionic ligand.

16. The composition of claim 11, wherein z=2 or 4 and at least one of L'' is an anionic ligand.

17. The composition of claim 11, wherein the composition is selected from the group of compositions represented by structures VI-VII:

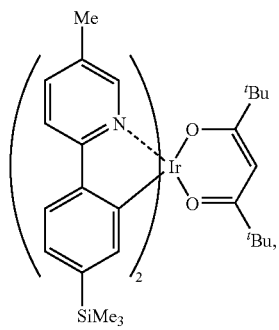

Structure VI

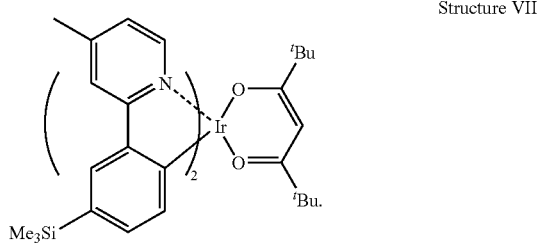

Structure VII

* * * * *